United States Patent
Oreffo et al.

(10) Patent No.: US 12,036,328 B1
(45) Date of Patent: Jul. 16, 2024

(54) CLAY NANOPARTICLES FOR MEDICAL USE

(71) Applicant: Renovos Biologics Limited, Southampton (GB)

(72) Inventors: Richard Oreffo, Southampton (GB); Jonathan Dawson, Southampton (GB); Mohamed Mousa, Southampton (GB); Allison Shaw, Southampton (GB); Agnieszka Janeczek, Southampton (GB)

(73) Assignee: Renovos Biologics Limited, Southampton (GB)

( * ) Notice: Subject to any disclaimer, the term of this patent is extended or adjusted under 35 U.S.C. 154(b) by 0 days.

(21) Appl. No.: 18/491,443

(22) Filed: Oct. 20, 2023

(30) Foreign Application Priority Data

Dec. 22, 2022 (EP) .................................. 22216031

(51) Int. Cl.
*A61K 9/51* (2006.01)
*A61K 9/06* (2006.01)
*A61K 38/18* (2006.01)
*A61K 45/06* (2006.01)

(52) U.S. Cl.
CPC .............. *A61K 9/5115* (2013.01); *A61K 9/06* (2013.01); *A61K 38/1875* (2013.01); *A61K 45/06* (2013.01)

(58) Field of Classification Search
CPC .................................................... A61K 9/5115
See application file for complete search history.

(56) References Cited

U.S. PATENT DOCUMENTS

| | | |
|---|---|---|
| 3,666,407 A | 5/1972 | Orlemann |
| 3,671,190 A | 6/1972 | Neumann |
| 4,040,974 A | 8/1977 | Wright |
| 4,049,780 A | 9/1977 | Neumann |
| 6,890,502 B2 | 5/2005 | Bauer |
| 10,245,350 B2 | 4/2019 | Oreffo |
| 10,882,752 B2 | 1/2021 | Kim |
| 2022/0041458 A1 | 2/2022 | Lu |

FOREIGN PATENT DOCUMENTS

| | | |
|---|---|---|
| EP | 0614445 | 9/1994 |
| GB | 1537766 | 1/1979 |
| WO | 2020132216 | 6/2020 |

OTHER PUBLICATIONS

Gibbs et al. (Bone induction at physiological doses of BMP through localization by clay nanoparticle gels, Biomaterials, 2016) (Year: 2016).*
Ruzicka et al. (A fresh look at the Laponite phase diagram, Soft Matter, 2010) (Year: 2010).*
Au et al. (Behavior of Laponite gels: Rheology, ageing, pH effect and phase state in the presence of dispersant, Chemical Engineering Research and Design, 2015) (Year: 2015).*
Mohanty et al. (Chemical stability phase diagram of aqueous Laponite dispersions, Applied Clay Science, 2016) (Year: 2016).*
Gentile et al., Nanotechnology, vol. 26 No. 42, 2015, p. 422001.
Murali et al., Materials Today, vol. 50, 2021, pp. 276-302.
Mousa et al., Biomater. Sci, vol. 9, 2021, pp. 3150-3161.
Neumann and Sansom, Clay Minerals, vol. 9 No. 2, 1971, pp. 231-243.
"Silicate(2-), hexafluoro-, disodium, reaction product with lithium magnesium sodium silicate"—ECHA—https://echa.europa.eu/brief-profile/-/briefprofile/100.077.563 (last updated Nov. 1, 2023).
Mohammed Mousa (2020) "Elucidating Nanoclay-Stem Cell Interactions for Enhancing Bone Regeneration", University of Southampton, Faculty of Engineering and Physical Sciences, Bioengineering Unit, PhD Thesis.
European Search Report EP22216031 dated Mar. 7, 2023.

* cited by examiner

*Primary Examiner* — Andrew S Rosenthal
*Assistant Examiner* — Danielle Kim
(74) *Attorney, Agent, or Firm* — PABST PATENT GROUP LLP

(57) ABSTRACT

Compositions, processes, and methods are provided including, but not limited to, a composition including a plurality of clay nanoparticles, wherein each clay nanoparticle comprises an anionic component and a cationic component wherein the anionic component has the formula (I):

$$[(Si_8Mg_bLi_c)O_{20}(OH)_4] \qquad (I)$$

wherein $5.5 < b \leq 6$,
and wherein $c > 0$ and $b/c > 12$.

21 Claims, 8 Drawing Sheets

5A

5B

5C

CLAY NANOPARTICLES FOR MEDICAL USE

CROSS-REFERENCE TO RELATED APPLICATIONS

This application claims the benefit of and priority to EP22216031, filed Dec. 22, 2022, which is hereby specifically incorporated by reference in its entirety.

FIELD OF THE INVENTION

The invention relates to compositions including clay nanoparticles, methods for making such compositions and their use in medical and cosmetic methods. The nanoclays can be used alone or in combination with therapeutic or diagnostic agents. For example, the nanoclays can be used in the delivery of therapeutic or diagnostic agents or in regenerative medicine.

BACKGROUND

Clay nanoparticles are nanoparticles of layered mineral silicates that have numerous applications including in cosmetics and paints. Clay nanoparticles have also been used in the pharmaceutical industry as excipients and active agents. Depending on chemical composition, crystallographic structures and nanoparticle morphology, clay nanoparticles are organised into several classes such as montmorillonite, bentonite, smectite, kalinite, hectorite, and halloysite.

Certain clay nanoparticles self-assemble into a gel in an aqueous environment, for example in the body, and the resulting nanoclay gels have been found to be particularly well suited to providing a regenerative microenvironment, or a platform for drug delivery. An example of a nanoclay that has been used in medical and cosmetic formulations is Laponite™ (a synthetic smectite clay manufactured by BYK). Laponite™ is a disc-shaped synthetic hectorite type clay which has been cited as a potential nanomedicine for use in drug delivery, bio-imaging, tissue engineering and regenerative medicine.

Important features of some nanoclay gels when used as a nanomedicine include ease of administration and high stability in vivo, post administration. A high stability is desired such that, once the gel is situated at the target site, it provides a stable matrix structure into which new cells can grow, or from which drugs can be delivered. Poor stability at the target site can lead to the nanoclay gel becoming dispersed throughout the subject, meaning it does not serve its intended purpose in the correct location, and can cause potentially harmful effects elsewhere in the body.

There is a need therefore, for clay nanoparticle gels which can be effectively localised at a target site and have high stability under physiological conditions (i.e. pH 7.35 to 7.45, and 36.1° C. to 37.5° C.) and which can be safely and conveniently administered and retained to a subject. Current known clay nanoparticles do not meet these requirements.

Some attempts have been made to address the issues relating to gel stability by creating organo-nanoclay composites. However, these employ cross-linkable polymer chemistry which is complex, hard to regulate, and extremely time sensitive. For clinical viability, more reliable formulations, which can easily be manufactured are desirable.

Results show that clear gels which have a high stability in vivo can be produced from clay nanoparticles having an increased ratio of magnesium ions to lithium ions within the clay nanoparticles, compared to existing nanoclays. Nanoclay gels produced from such particles can have good rheological properties, and in particular exhibit a change in rheological properties in physiological conditions, thus facilitating administration of the gels by injection, whilst providing a clear and stable gel at physiological pH. In addition, the formulations including the clay nanoparticles of the disclosure can self-assemble, and can easily be manufactured.

SUMMARY OF THE INVENTION

Compositions, process, and methods including, but not limited to, a composition including a plurality of clay nanoparticles, wherein each clay nanoparticle includes an anionic component and a cationic component wherein the anionic component has the formula (I):

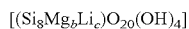

$$[(Si_8Mg_bLi_c)O_{20}(OH)_4] \quad (I)$$

wherein $5.5 < b \leq 6$, and wherein $c > 0$ and $b/c > 12$

It has been found that the gel compositions described herein have high stability at physiological pH. Such gels can be easily administered, typically by a syringe, without causing significant discomfort or distress to a subject. Further, the gels stabilise in physiological conditions, ensuring effective localisation at the target site and reducing undesired effects caused by delocalisation of the gel.

Also provided is a process for making a composition of the disclosure wherein the process includes combining a lithium salt solution, a magnesium salt solution, a solution including the cationic component, and a silicate solution, and heating the solutions together until a slurry is formed.

Further provided are compositions as disclosed herein for use in the treatment of the human or animal body by therapy or diagnosis, in particular by therapy. In particular, the composition can be for use in a method of tissue repair and/or regeneration, and/or a method of cell delivery. The composition can also be for use in the treatment or prevention of infection.

The composition can be used in cosmetic methods. In some embodiments, the composition is a cosmetic composition, in particular a tissue filler or a topical gel or cream.

The disclosure also provides a composition for use in a method of delivery of one or more therapeutic or diagnostic agents to a target site in the human or animal body, wherein said method includes administering said composition to the human or animal body.

BRIEF DESCRIPTION OF THE FIGURES

References in the Figures to Renovite, Renovite 1.0 or Renovite analogues refer to the disclosed compositions, unless otherwise specified.

DETAILED DESCRIPTION OF THE INVENTION

Clay Nanoparticles for Medical Use

Figure 1:
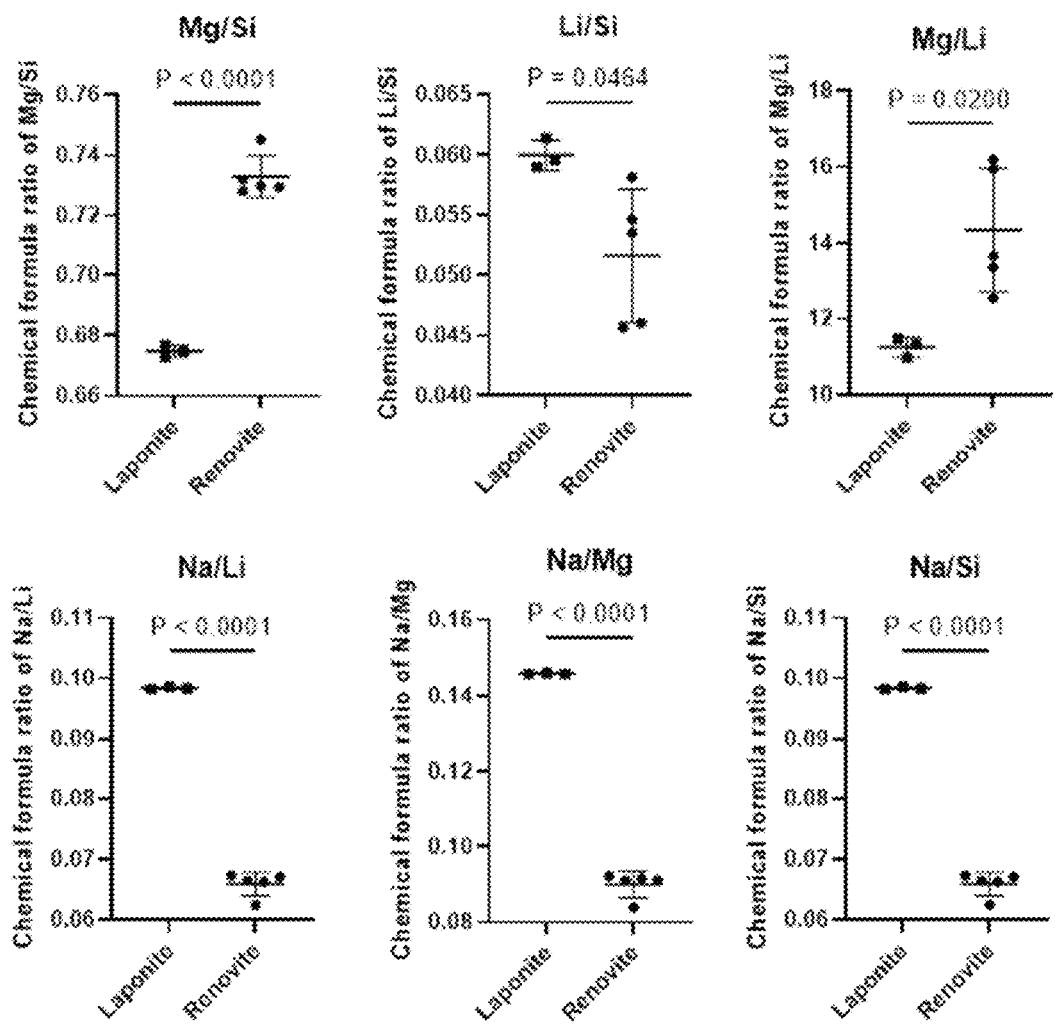
FIG. 1 shows the comparison of elemental ratios between Laponite™ XLG and the compositions of the disclosure set out in Table 1 (Renovite). Empirically determined Mg, Li and Na are presented relative to empirically determined Si scaled according to $(Na_{+a}[(Si_8Mg_bLi_d)O_{20}(OH)_4]^{-a}$. Bars represent mean and SD. P values calculated using an unpaired T-test.

A clay nanoparticle as described herein is an inorganic nanoparticle. A clay nanoparticle can include or consist of a silicate. The silicate can include layered silicate.

The clay nanoparticles can have an average size of from about 15 nm to about 50 nm in the longest dimension. The clay nanoparticles can have an average size of from about 20 nm to about 40 nm in the longest dimension. For example, the clay nanoparticles can have an average size of from about 15 nm to about 40 nm, or from about 20 nm to about 50 nm, or from about 24 nm to about 36 nm in the longest dimension.

The clay nanoparticles can have an average thickness (shortest dimension) of from about 1 nm to about 3 nm. For example, the clay nanoparticles can have an average thickness of from about 1 nm to about 2.5 nm, or from about 1.5 nm to about 2.5 nm, or from about 1.3 nm to about 2.2 nm.

The dimensions of the clay nanoparticles can be determined by any appropriate method known to the skilled person. Typically the dimensions are determined using small-angle X-ray scattering. The dimensions of the clay nanoparticles can be determined when dispersed in an aqueous environment.

The clay nanoparticles can have an aspect ratio of at least 1:5. For example, the clay nanoparticles can have an aspect ratio of at least 1:10, or at least 1:20, or at least 1:25. The clay nanoparticles can have an aspect ratio of less than 1:100. For example, the clay nanoparticles can have an aspect ratio of less than 1:50, or less than 1:30. The clay nanoparticles can have an aspect ratio of from 1:10 to 1:50. For example, the clay nanoparticles can have an aspect ratio of from 1:5 to 1:30 or from 1:10 to 1:30.

Each clay nanoparticle of the disclosure includes an anionic component and a cationic component. The anionic component has the formula (I):

$$[(Si_8Mg_bLi_c)O_{20}(OH)_4] \qquad (I)$$

The anionic component of the clay nanoparticle carries a negative charge. Typically this negative charge is a−, wherein a is equal to the positive charge carried by the cationic component. a is greater than 0, and is not necessarily an integer value.

b, in the above formula (I) represents the number of Mg atoms present per unit of the anionic component. b is not necessarily an integer value. b is typically ≤6.0. More typically, b≤5.9. b is typically ≥5.6, preferably 5.5≤b≥6.0, for example 5.6≤b≥6.0 or 5.6≤b≥5.9.

c in the above formula (I) represents the number of Li atoms present per unit of the anionic component. c is greater than 0, and is not necessarily an integer value. c is typically ≤2, more typically ≤1. Preferably c is ≤0.5, more preferably c≤0.45, for example c can be ≤0.4 or ≤0.35, such as ≤0.33. c is typically ≥0.2, more typically ≥0.3. Therefore, 0<c≤2, 0<c≤1, 0<c≤0.5, 0<c≤0.4, 0.2≤c≤2, 0.2≤c≤1, 0.2≤c≤0.5, 0.2≤c≤0.45, 0.3≤c≤0.5, 0.3≤c≤0.45, 0.3≤c≤0.4.

Or typically, $0.2 \leq c \leq 0.35$, or $0.2 \leq c \leq 0.33$. In some preferred embodiments $0.2 \leq c \leq 0.5$, in particularly preferred embodiments $0.3 \leq c \leq 0.5$.

The ratio b/c is greater than 12. Typically the ratio is less than 100, such that typically $12 < b/c \leq 100$. In some embodiments, b/c is $\geq 13$. In some embodiments, $b/c \geq 14$. b/c is typically $\leq 18$, such as $b/c < 18$, or $b/c \leq 17$. In some preferred embodiments $b/c \leq 16$. Therefore preferably, $12 < b/c \leq 18$, preferably from $12 < b/c < 18$, more preferably $12 < b/c \leq 17$. In some embodiments, $13 \leq b/c \leq 18$, $13 < b/c < 18$, $13 \leq b/c \leq 17$, $13 \leq b/c \leq 16$, $14 \leq b/c \leq 18$, $14 < b/c < 18$, $14 \leq b/c \leq 17$ or $14 \leq b/c \leq 16$.

The figures b and c are preferably determined using elemental analysis using inductively coupled plasma-optical emission spectrometry (ICP-OES). Example 2 described herein provides further details of a suitable method for determining these values using elemental analysis.

The cationic component of each clay nanoparticle typically includes one or more metal cations. In some embodiments the cationic component includes one or more metal cations selected from alkali metal cations, alkaline earth metal cations, transition metal cations and combinations thereof. Such metal cations can include one or more cations of lithium, sodium, calcium, copper, potassium or magnesium. Sodium is preferred.

Typically the metal cation can be of the formula $M^{n+}$, wherein M is a metal and n is an integer, typically an integer from 1 to 6, more typically from 1 to 4. Preferably n is 1 or 2, more preferably 1. $M^{n+}$ is preferably $Na^+$.

Therefore, typically the clay nanoparticle includes an anionic component and a cationic component such that the clay nanoparticle has the formula:

$$[(M^{n+})_x(M2^{p+})_y][(Si_8Mg_bLi_c)O_{20}(OH)_4]^{a-}$$

wherein b, c and a are as defined anywhere herein, and wherein $M^{n+}$ and $M2^{p+}$ are different metal cations, and n and p are the same or different and are integers of from 1 to 6, typically 1 or 2. Typically the charge is balanced such that nx+py=a. x and y need not be integers, and can be the same or different. The sum of x and y is greater than 0. Typically the sum of x and y (i.e. x+y) is $\leq 2$, more typically $\leq 1$. In some preferred embodiments x+y is $\leq 0.7$ more preferably x+y is $\leq 0.5$. Typically x+y is $\geq 0.3$, more typically $\geq 0.4$. Therefore, in some embodiments, $0 < (x+y) \leq 2$, such as $0 < (x+y) \leq 1$, $0 < (x+y) \leq 0.7$, $0 < (x+y) \leq 0.5$, $0.2 \leq (x+y) \leq 0.7$, $0.3 \leq (x+y) \leq 0.7$, $0.4 \leq (x+y) \leq 0.7$, $0.3 \leq (x+y) \leq 0.5$, or $0.4 \leq (x+y) \leq 0.5$. In some preferred embodiments $0.2 \leq (x+y) \leq 0.7$, more preferably wherein $0.3 \leq (x+y) \leq 0.5$.

In some embodiments the cationic component of the clay includes only one type of metal cation, such that the clay nanoparticle has the formula:

$$(M^{n+})_z[(Si_8Mg_bLi_c)O_{20}(OH)_4]^{a-}$$

wherein n is an integer from 1 to 4, typically 1 or 2, more typically 1, and z is equal to a/n. In some preferred embodiments M" is Nat, such that the clay nanoparticles has the formula:

$$(Na^+)_a[(Si_8Mg_bLi_c)O_{20}(OH)_4]^a$$

wherein a, b, and c are as defined anywhere herein.

The nanoparticles of the disclosure can contain impurities and/or by-products. The nanoparticles are preferably 90% pure, more preferably 95% pure, more preferably 98% or 99% pure. Most preferably, the nanoparticles are substantially pure particles of formula $[(Si_8Mg_bLi_c)O_{20}(OH)_4]$ as defined herein.

Compositions of the Disclosure

A composition of the disclosure includes a plurality of clay nanoparticles, wherein each clay nanoparticle includes an anionic component and a cationic component wherein the anionic component has the formula (I):

$$[(Si_8Mg_bLi_c)O_{20}(OH)_4] \qquad (I)$$

wherein $5.5 < b \leq 6$, and wherein $c > 0$ and $b/c > 12$.

Herein a plurality of clay nanoparticles refers to two or more clay nanoparticles.

A composition of the disclosure can contain up to 100 wt % of the clay nanoparticles of the disclosure. More typically, it contains up to 85 wt % of the clay nanoparticles of the disclosure, or up to 50% wt of the clay nanoparticles of the disclosure. Typically, the composition contains at least 0.1 wt % clay nanoparticles, e.g. from 0.1 to 100 wt %, 0.1 to 85 wt % or 0.1 to 50 wt %.

The clay nanoparticles described herein can include coordinated water. Reference herein to clay nanoparticles of the disclosure is therefore intended to encompass clay nanoparticles having coordinated water. Further, reference herein to dried compositions is intended to encompass compositions including clay nanoparticles which include coordinated water. Therefore, a dried composition can contain up to 10 wt % water. More typically it contains up to 7 wt % water. Typically the composition contains at least 3 wt % water, or at least 5 wt % water. Typically, therefore, the composition can include from 3 wt % to 10 wt % water, such as from 5 wt % to 7 wt % water. In such embodiments, the remainder of the composition can contain up to 100 wt % clay nanoparticles of the disclosure, such that the composition contains, for example, 93 wt % to 95 wt % clay nanoparticles of the disclosure.

The composition can consist of, or consist substantially of, the clay nanoparticles of the disclosure. In such embodiments, the composition is typically in dried form, e.g. a powder, a film, granules, a coating, porous sponge, or fibres. The composition can for example include at least 90% clay nanoparticles, at least 95% clay nanoparticles, at least 98% or 99% clay nanoparticles or about 99.5% clay nanoparticles. Alternatively, additional materials can be present in the composition, for example including carriers or diluents (e.g. water or saline), excipients and/or therapeutic or diagnostic agents. In embodiments wherein the composition is in a powder form, for example, the composition can further include additional materials such as ions, proteins, and polymers.

In some preferable embodiments the composition of the disclosure is in dried form, e.g. in the form of a powder. The composition can be lyophilised, e.g. a lyophilised powder. An alternative dried form is a film. In some embodiments, e.g. where water or saline is present in the composition, the composition is a liquid-solid fluid mixture such as a slurry, or a paste. In some embodiments, e.g. where water or saline is present in the composition, the composition is in the form of a gel. A gel is a preferred form of the composition of the disclosure and the compositions are typically administered in this form.

A gel of the disclosure can be formed, for example, by casting the clay nanoparticles in water. A gel of the disclosure can be dried to form a film, or lyophilised. Where the composition is provided as a film or in lyophilised form, it can be administered by application to a surface. Alternatively, it can be reconstituted with a diluent, such as water or saline, before use.

The composition can be a pharmaceutical composition, which is a composition suitable for pharmaceutical use. A pharmaceutical composition typically includes one or more pharmaceutically acceptable excipients. Preferred pharmaceutical compositions are sterile and pyrogen free.

Suitable carriers and/or diluents for use in the disclosure include pharmaceutically acceptable carriers such as water and aqueous solutions, in particular saline. Isotonic solutions, in particular isotonic saline, are preferred. The carrier or diluent is typically sterile. Thus, sterile, isotonic saline is a preferred carrier. Such carriers can be used in the case of compositions which are in the form of a slurry or a gel.

Excipients can also be included in the composition, as needed. The skilled person would be familiar with suitable excipients that can be useful to include. In one embodiment, where the composition further includes a therapeutic and/or diagnostic agent, for example, a second carrier material for the therapeutic or diagnostic agent can be used. The second carrier can be a polymeric material. In some preferred embodiments the second carrier is selected from carboxymethylcellulose, gelatine and collagen.

For solid form drugs: diluents e.g. lactose, dextrose, saccharose, cellulose, corn starch or potato starch; rheology modifiers, such as carboxymethylcellulose, gelatine and collagen; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; wetting agents, such as lecithin, polysorbates, laurylsulphates; dispersants, such as sodium polyacrylate and pyrophosphates; and, in general, non toxic and pharmacologically inactive substances used in pharmaceutical formulations.

For liquid forms such as syrups: rheology modifiers, such as carboxymethylcellulose, gelatine and collagen; carriers, for example, saccharose or saccharose with glycerine and/or mannitol and/or sorbitol.

For suspensions and emulsions: carriers, for example a natural gum, agar, sodium alginate, pectin, methylcellulose, carboxymethylcellulose, or polyvinyl alcohol.

For injectable forms, as well as sterile water which is mentioned already above: rheology modifiers, such as carboxymethylcellulose, gelatine and collagen; olive oil; ethyl oleate; glycols, e.g. propylene glycol; and if desired, a suitable amount of lidocaine hydrochloride.

Preferred compositions of the disclosure include the nanoparticles of the disclosure and water, wherein the nanoparticles are present in an amount of from about 0.1 wt % to about 50 wt % based on the total weight of the composition. Preferred compositions include from about 0.5 wt % to about 40 wt % nanoparticles of the disclosure, based on the total weight of the composition. For example, the composition can include from about 1 wt % or from about 2 wt % and up to about 40 wt % nanoparticles of the disclosure. The composition typically also includes water or saline. The composition can optionally include one or more further additives. The composition can consist of, or consist essentially of, the nanoparticles of the disclosure and water or saline.

A preferred composition of the disclosure is a gel, particularly a pharmaceutically acceptable gel. A gel typically includes the nanoparticles of the disclosure in an amount of from about 2 wt % to about 12 wt %, based on the total weight of the gel. The gel can further include water in an amount of from about 80 wt % to about 98 wt %, for example from about 85 wt % to about 96 wt % or from about 88 wt % to about 94 wt %.

Where a gel includes the nanoparticles of the disclosure in an amount above 7 wt %, the nanoparticles can not adequately disperse. In this case, the gel can also include a dispersant such as pyrophosphate or sodium polyacrylate. In embodiments where a dispersant is present in the gel, the gel can include the nanoparticles of the disclosure in an amount of up to around 12 wt % of the total weight of the gel. For example, where a dispersant is present, the gel can include the nanoparticles of the disclosure in an amount of from about 2 wt % to about 12 wt %, from about 4 wt % to about 10 wt %, or from about 7 wt % to about 10 wt %. Such a gel can further include water in an amount of from about 80 wt % to about 98 wt %, for example from about 85 wt % to about 96 wt % or from about 88 wt % to about 93 wt %.

Compositions which do not include a dispersant, e.g. a composition which consists of or substantially consists of nanoparticles of the disclosure and water, typically forms a gel when the nanoparticles are present in an amount of up to about 7 wt % based on the total weight of the gel. Accordingly, in embodiments where a dispersant is not present, for example where the composition consists of, or substantially consists of the nanoparticles of the disclosure and water, the gel typically includes nanoparticles of the disclosure in an amount of about 2 wt % to about 7 wt % of the total weight of the gel. Often the gel includes the nanoparticles of the disclosure in an amount of from about 2 wt % to about 4 wt % of the total weight of the gel. In one embodiment, the gel includes the nanoparticles of the disclosure in an amount of from about 4 wt % to about 5 wt %. In another embodiment, the gel includes the nanoparticles of the disclosure in an amount of from about 5 wt % to about 6 wt %. The water content of the gel can in this case be from about 93 wt % to about 98 wt %, such as from about 96 wt % to about 98 wt %, based on the total weight of the gel.

The composition of the disclosure can alternatively be a paste. Typically when the composition is a paste, the composition includes the nanoparticles of the disclosure in an amount of from 7 wt % to 50 wt % of the total weight of the composition, such as from 10 wt % to 40 wt %, or from 20 wt % to 30 wt %.

The composition of the disclosure can alternatively be a sol. Typically when the composition of the disclosure is a sol, the composition includes the nanoparticles of the disclosure in an amount of from 0.1 wt % to 2% of the total weight of the composition, such as from 0.5 wt % to 2 wt %, or from 1 wt % to 2 wt %.

The compositions of the disclosure are typically biodegradable. The term biodegradable is understood to mean that the composition has the ability to break down over time in the tissue or body of a human or animal and/or in the environment. The time for complete degradation can be at least 1 week, at least one month, at least 2 months, at least 6 months or at least 12 months. The time for complete degradation can be no more than 12 months or no more than 6 months. For example, the time for complete degradation can be from 1 week to 12 months, 1 week to 6 months, 1 month to 12 months, 1 month to 6 months, 2 months to 12 months or 2 months to 6 months. The degradation time can affect the speed at which drug is released from the gel when in situ in the body. Therefore, the degradation time be desirably varied depending on any therapeutic or diagnostic agent which is present in the composition.

When the composition is a gel, the gel preferably demonstrates a 50% change in zeta potential within a pH range of from pH 6.5 to pH 8. A 50% change in zeta potential is defined as a change of measured zeta potential of at least 50% compared with the baseline zeta potential, on titration with acid. Baseline zeta potential is the zeta potential of the gel without pH modification, i.e. before addition of acid.

Baseline zeta potential is typically that measured at pH 9 to pH 11, more typically from pH 9.5 to pH 10.5, more typically about pH 10.

The change in zeta potential is typically a reduction of the magnitude of the zeta potential value, i.e. the absolute value of the zeta potential moves towards zero. This indicates an increase in stability of the gel. The zeta potential value can be positive or negative. A reduction in the absolute value in either case indicates that the value is closer to zero.

Preferably, the 50% change in zeta potential occurs at a pH range of from pH 7 to pH 7.8, more preferably at a pH range of from pH 7.2 to pH 7.8. In particularly preferred embodiments, the 50% change in zeta potential of the gel occurs in a pH range of from pH 7.3 to pH 7.5.

Typically, the change in zeta potential is measured via titration of the gel with an acid, such as hydrochloric acid. Zeta potential change can be determined using any appropriate method known in the prior art. For example it can be determined using equipment designed for measuring zeta potential, such as a Stabino Zeta™ kit. Typically the zeta potential is measured using a solution of nanoparticles in water, typically a 1 wt % solution of nanoparticles in ultrapure water. The zeta potential is a measure of the electrokinetic potential of particles in a colloidal system and can be used as an indication of the stability of the gel. Particles having a large negative zeta potential will tend to repel one another. However, a low negative zeta potential indicates that there is little repulsion between the particles. The particles of the disclosure therefore preferably have a negative zeta potential, wherein the value is <50% of the absolute value, at a pH in physiological range. This means that the gel is at its most stable in the region of physiological pH.

The gels of the disclosure typically have a pH of around 10 in the absence of rheological or pH modifiers. At this pH, the gels typically have very large negative zeta potential, meaning the particles repel one another and are more flowable, and therefore relatively easy to administer, for example by injection. However, on contact with bodily fluids or other physiological pH environment, a change in zeta potential occurs, typically reducing the repelling forces between particles. The stability or stiffness of the gel therefore increases, thus providing a stiffer, more stable gel at the site at which it is delivered. This further gelation may be a result of new attractive interactions as a result of increased ionicity. Further, when in contact with bodily fluids, proteins that diffuse into the gel may bind and form bridges between particles to further stabilise the gel. The increase in stability helps to retain the gel at the site of administration and avoid off-target side effects.

Therapeutic or Diagnostic Agents

The composition of the disclosure can further include one or more therapeutic or diagnostic agents. A therapeutic or diagnostic agent can be a small molecule therapeutic or diagnostic agent, including small molecule drugs, prodrugs, or dyes or colourants. A therapeutic or diagnostic agent can alternatively be a biologic, wherein a biologic can be an amino acid, signalling molecule, peptide, protein (wherein the protein can be a recombinant protein or a native protein), antibody, nucleic acid, oligonucleotide (such as an aptamer), or cell. A therapeutic or diagnostic agent can alternatively be a polymeric material. Combinations of one or more therapeutic or diagnostic agent can be used.

The nanoclay compositions of the disclosure can be used for the delivery of a wide variety of different therapeutic or diagnostic agents and the nature of the agent(s) used is not particularly limited. Exemplary therapeutic agents include antimicrobial agents (for example antibiotics), growth factors, antibodies, nutrients, enzymes, hormones, steroids, biological tissue substitutes, synthetic tissue substitutes, aptamers and cells. Exemplary diagnostic agents include dyes, colourants, radioisotopes (which can be for X-ray detection and or monitoring of degradation), contrast agents (such as contrast agents for CT, such as iodine containing contrast agents and barium sulfate; contrast agents for MRI, such as gadolinium (III), iron oxide, iron platinum and manganese; or contrast agents for ultrasound), or fluorescent molecules. A combination of two or more therapeutic agents can be used. A combination of two or more diagnostic agents can be used. One or more therapeutic agents can be used in combination with one or more diagnostic agents.

In one embodiment, the one or more therapeutic or diagnostic agents are agents which are useful in regenerative medicine. In some embodiments, the one or more therapeutic or diagnostic agents are selected from growth factors, antibodies, biological tissue substitutes, synthetic bone grafts and cells. Antimicrobial agents can be included in the composition in addition or instead of such therapeutic agents. Any antimicrobial agent can be used. Examples include antibiotics such as vancomycin, gentamycin, tobramycin and chlorhexidine.

Typically a biological tissue substitute can be a substitute for a soft tissue such as bone marrow or plasma or a substitute for a hard tissue such as bone. Examples of biological tissue substitutes include platelet rich plasma (PRP) and biological bone-graft substitute.

Typically a synthetic tissue substitute can be a synthetic bone graft. Synthetic bone grafts include calcium salts such as calcium sulfates or calcium phosphates, alone or in combination. β-tricalcium phosphate (β-TCP) is a preferred calcium phosphate. Hydroxyapatite (HA) is a further preferred calcium phosphate.

Typically a cell can be a somatic cell, such as a chondrocyte; a progenitor cell; or a stem cell, such as a mesenchymal stem cell. Cells can also be provided as bone marrow aspirate (BMA).

Typically, a protein is a recombinant protein. Any protein for use in regenerative medicine can be used. Typically a recombinant protein is a growth factor, such as a bone morphogenetic protein (BMP), platelet derived growth factor (PDGF), transforming growth factor (TGF), fibroblast growth factor (FGF), vascular endothelial growth factor (VEGF), or insulin like growth factor (IGF). A combination of two or more such growth factors can be used.

An aptamer, as referred to herein, is a short synthetic ssDNA or ssRNA sequence. An aptamer can be a therapeutic, or a diagnostic aptamer, such as an aptamer which interacts with a biomarker. Such an aptamer can further include a diagnostic feature, such as a fluorescent marker, or a radioisotope.

In some preferred embodiments the composition includes BMP, or a BMP analogue such as AMP. BMP-2, BMP-3, BMP-4, BMP-6, BMP-7, and BMP-8 or heterodimers of thereof. AMP-2 is an example of a suitable analogue of BMP-2. More preferably, the composition includes BMP-2 and/or BMP-7 and analogues thereof, in particular BMP-2 and/or BMP-7. Most preferably the composition includes BMP-2 and analogues thereof, in particular BMP-2.

The one or more therapeutic or diagnostic agents can alternatively be for use in treating or diagnosing diseases and disorders other than those relevant to regenerative medicine. For instance, the composition of the disclosure can be for use in delivering therapeutic and/or diagnostic agents suitable for treating or diagnosing cancer. For example, diagnostic agents which exhibit chemiluminescence, fluorescence, or contain radioactive isotopes can be used. Suitable therapeutic agents include one or a combination selected from doxorubicin, β-lapachone, or methotrexate.

The composition typically includes a diagnostically visible and/or therapeutically effective amount of the one or more diagnostic or therapeutic agents respectively. This amount could be determined by the skilled person in the art based on the nature of the drug and the size and weight of the subject.

In an embodiment where BMP is provided as a therapeutic agent the BMP can be provided at a dose of from about 0.01 µg to about 50 mg, for example from about 0.1 µg to about 20 mg, or from about 1 µg to about 15 mg total dose. The skilled person will understand that the dose can be dependent on the clinical context, such as the size of the area to be treated or the total volume of the composition.

The use of clay nanoparticles for BMP delivery provides dosing control, allowing low doses of BMP (e.g. from 0.1 to 300 µg) to be used to encourage bone formation at a defect, or allowing higher doses (e.g. from 10 µg to about 25 mg, or from 300 µg to about 15 mg) to be used with reduced risk of off-target effects. Studies have demonstrated significant adverse effects with higher dose BMP use and its poor local retention such as: heterotopic ossification, osteolysis, and swelling. Therefore, allowing low dosages of BMP or ensuring retention of the protein at the target site, facilitates fracture healing and arthrodesis without precipitation of serious adverse effects. Targeted administration of BMP, as facilitated by the high stability and stiffness of gels provided by the present disclosure, also reduces off-target, adverse side-effects of BMP.

When the composition includes one or more therapeutic and/or diagnostic agent(s), the therapeutic and/or diagnostic agent(s) can be provided in combination with a pharmaceutically acceptable carrier, referred to herein as a second carrier. Any suitable drug carrier can be used and the skilled person would be familiar with the selection of suitable carriers and excipients for the therapeutic and diagnostic agents which can be used in the present disclosure. Typically a carrier can be selected from carboxymethylcellulose, gelatine and collagen. Further excipient(s) can optionally be incorporated.

In some embodiments, the composition does not include a further diagnostic and/or therapeutic agent.

Kits

Also provided herein are kits including the compositions or pharmaceutical compositions according to the disclosure.

In some embodiments a kit of the disclosure includes a syringe, e.g. a pre-filled syringe wherein the syringe contains a composition as described herein wherein the composition is in the form of a gel. In some embodiments a kit can include separately a syringe and a composition of the disclosure. In such embodiments the composition can be in a gel form, stored in a container such as a pouch. In other such embodiments, the composition can be in a form which can be a precursor to a gel form, typically solid form, such as a powder, typically a lyophilised powder, which can be hydrated to form a gel.

In some embodiments, a kit of the disclosure includes a vial, which can be a sprayable vial, e.g. a pre-filled vial containing a composition of the disclosure as described herein.

In some embodiments a kit of the disclosure can include one or more therapeutic or diagnostic agents as defined anywhere herein. The therapeutic and/or diagnostic agent(s) can be provided separately from the composition of the disclosure, or they can be provided within the composition of the disclosure.

Preferably the composition is in powder form or in the form of a gel; and/or the therapeutic or diagnostic agent(s) are in a powder form. When the composition is in a powder form, use of the kit can involve the powder being hydrated to form a gel.

The composition of the disclosure and the therapeutic and/or diagnostic agent(s) can be provided in a form suitable for separate administration.

Alternatively, the one or more therapeutic and/or diagnostic agent(s) can be provided in a form suitable for addition to the gel prior to administration to a subject. Alternatively, the drug and the composition can be premixed in dried form and use of the kit can involve hydration of the mixture to form a gel suitable for administration.

A kit can include a biological implant, and the composition of the disclosure. In one embodiment, the biological implant is pre-coated with a gel or a dried film, as described herein. Alternatively, the composition (e.g. a gel or a dried film) and the implant can be provided separately. A biological implant, as referred to herein can be a medical device, such as a pace maker, implantable defibrillator or contraceptive implant; or a prosthetic implant, such as a knee, hip, or shoulder replacement, or medical screw or other fixator.

A kit can include the gel of the disclosure in the form of a dehydrated film. The kit can further include equipment for hydrating the film. The use of such a kit can involve administration of the film, for example by application onto the skin, and subsequent hydration of the film.

In some embodiments a kit can include the composition in the form of granules, or microparticles.

The kit can also include instructions for use.

Therapeutic Uses

The composition as described anywhere herein can be for use in the treatment of the human or animal body.

In one aspect, the subject is a mammal, in particular a human. However, it can be non-human. Preferred non-human animals include, but are not limited to, primates, such as marmosets or monkeys, commercially farmed animals, such as horses, cows, sheep or pigs, and pets, such as dogs, cats, mice, rats, guinea pigs, ferrets, gerbils or hamsters.

In one embodiment, the composition is for use in a method of regenerative medicine.

Therefore the disclosure also provides the use of a composition of the disclosure for the manufacture of a medicament for use in a method of regenerative medicine.

The disclosure also provides a method of regenerative medicine, including administering to a subject an effective amount of a composition of the disclosure.

As described herein regenerative medicine includes tissue repair and regeneration, wherein tissue repair and regeneration can include tissue formation and/or fusion. This can include repair or regeneration of soft tissues, wherein soft tissues include muscle (smooth muscle, skeletal muscle and cardiac muscle), fat, fibrous tissue (connective tissue, cartilage, tendons and ligaments), synovial tissue, blood vessels (arteries, veins and capillaries), lymph vessels, skin, and nerves. Regenerative medicine also includes repair and regeneration of hard tissues, wherein hard tissues include bone, tooth enamel, dentin and cementum.

Tissue repair and regeneration also includes tissue replacement, such as the filling of a void left by a tumour.

Preferably, the method of regenerative medicine is the repair or regeneration of skin, bone and/or cartilage.

A method of regenerative medicine can be a method of wound repair. For instance, the one or more drugs which can include the composition can be for use in wound repair, and to prevent or treat concurrent conditions often present in those who are in need of wound repair, for example inflammation, infection and pain.

In some instances, regenerative medicine can include cell delivery, such as delivery of cells to regenerate tissues, such as the delivery of somatic cells, such as chondrocytes; progenitor cells; or stem cells such as mesenchymal stem cells.

Therefore, the composition of the disclosure can be for use in a method of tissue repair or regeneration, and/or cell delivery.

Therefore the disclosure also provides the use of a composition of the disclosure for the manufacture of a medicament for use in tissue repair or regeneration, and/or cell delivery.

The disclosure also provides a method of tissue repair or regeneration, and/or cell delivery, wherein said method includes administering to a subject an effective amount of a composition of the disclosure.

In some instances, the composition of the disclosure can be for use in the treatment or prevention of infection.

Therefore, the disclosure also provides the use of a composition of the disclosure for the manufacture of a medicament for use in the treatment or prevention of infection.

The disclosure also provides a method of treating or preventing infection, wherein said method includes administering to a subject an effective amount of a composition of the disclosure.

The composition of the disclosure can also be for use in a method of delivery of one or more therapeutic or diagnostic agents to a target site in the human or animal body, wherein said method includes administering said composition to the human or animal body, wherein the composition includes one or more therapeutic or diagnostic agents and/or wherein one or more therapeutic or diagnostic agents are administered separately into the composition in vivo at the target site. The therapeutic or diagnostic agent for delivery can be any therapeutic or diagnostic agent as described herein. In some embodiments, the therapeutic or diagnostic agent is a cell. In some embodiments, the therapeutic or diagnostic agent is an agent useful in regenerative medicine. In some embodiments, the therapeutic or diagnostic agent is useful in the treatment of cancer, i.e. a cancer therapeutic such as doxorubicin, β-lapachone, or methotrexate. In such embodiments, the target site can typically be a tumour.

The compositions and pharmaceutical compositions of the disclosure can be administered in a variety of dosage forms. The compositions and pharmaceutical compositions of the disclosure can for example be administered parenterally, whether subcutaneously, intravenously, intramuscularly, intrasternally, or transdermally. Typically the compositions of the disclosure are administered by injection or are applied to an exposed target site. For example the composition can be administered directly to the surface of a subject to be treated, i.e. the surface is coated with a composition of the disclosure (e.g. by spray-coating a surface to be treated); or the composition is administered directly into a void in the subject's tissue, i.e. to fill or partially fill the void. Alternatively, the composition of the disclosure can be delivered via a fixed entry point, for example, via a cannula.

When the composition of the disclosure is in the form of a gel or dried film, it can be administered directly to a wound, e.g. a skin wound, or a burn, by covering the wound with the gel or film. Alternatively, the composition of the disclosure can be applied to a wound by spraying. A further dressing, such as a gauze and/or a bandage can then be applied. Alternatively, the gel or film can be incorporated in to the dressing, i.e. a bandage can include a gel or dried film of the disclosure.

The composition can also be provided as a coating on a medical device and provided to a subject together with the device. Rehydration of the composition can be carried out after the device is inserted, in the case of a composition provided as a dried film. Suitable medical devices include a pace maker, implantable defibrillator, or contraceptive implant; or a prosthetic implant, such as a knee, hip, or shoulder replacement, or medical screw or other fixator.

In embodiments where one or more therapeutic or diagnostic agents are used, the one or more therapeutic or diagnostic agent can administered as a single composition including the nanoparticles described herein and the therapeutic and/or diagnostic agent(s). Alternatively, the one or more therapeutic or diagnostic agents can be administered separately, subsequently or sequentially to administration of the gel. The separate, subsequent or sequential administration of the one or more therapeutic or diagnostic agents can include administration to the gel on a target surface or injection into the gel at the target site.

In such embodiments, the one or more therapeutic or diagnostic agents can be added in a therapeutically effective amount. The one or more therapeutic or diagnostic agents can be added in a single administration or via multiple administrations. In some embodiments the one or more therapeutic or diagnostic agents can be added in situ at a target site, to provide sustained delivery of the one or more therapeutic or diagnostic agents. The one or more therapeutic or diagnostic agents can be added in from 1 to 10 administrations, typically from 1 to 6 administrations, more typically from 1 to 4 administrations. There is no limit to the number of administrations that can be provided, provided the composition is not saturated. Therefore administration can continue until such a point as a subject's treatment has been completed.

In some embodiments the composition of the disclosure does not include any further therapeutic and/or diagnostic agents. In such embodiments, the composition can be administered via multiple administrations, such as from 1 to 10 administrations, typically from 1 to 6 administrations, more typically from 1 to 4 administrations.

When the one or more therapeutic or diagnostic agents are added to the composition in multiple administrations, there is no specific time lapse between each administration. The time lapse between each administration can be judged by the skilled person administering the one or more therapeutic or diagnostic agents and will depend on aspects such as the half-life of the therapeutic or diagnostic agent in question and the rate of release from the gel.

A therapeutically effective amount of a composition of the disclosure can be administered to a patient. A typical dose can be determined by the skilled person, according to the activity of the specific composition, the age, weight and conditions of the subject to be treated, the type and severity of the disease and the frequency and route of administration.

Cosmetic Uses

The composition as described anywhere herein can be used in cosmetic methods. Suitable methods include a method of hydrating the skin, improving the evenness of skin complexion, preventing or reducing wrinkles or skin embellishments, as a cosmetic topical cream or gel, or as a cosmetic tissue filler, such as a lip filler, or a dermal filler.

The methods can thus include administering a subject an effective amount of a disclosed composition to hydrate the skin, improve the evenness of skin complexion, and/or prevent or reduce wrinkles or skin embellishments. In some preferred embodiments, the composition is used as a cosmetic tissue filler. Alternatively, it can be used in a cosmetic topical cream.

Accordingly, the composition as described anywhere herein can be a cosmetic composition, which is a composition suitable for cosmetic use. A cosmetic composition typically includes one or more additives useful in formulating cosmetic compositions. The cosmetic composition can be a tissue filler, or a topical cream or gel.

Typically when the composition of the disclosure is a cosmetic composition, or used in a cosmetic method, it does not include a further diagnostic or therapeutic agent.

A cosmetic composition of the disclosure can optionally include an anti-inflammatory agent to reduce swelling. In some embodiments, anti-inflammatory agents are not present in a cosmetic composition. In some embodiments, a cosmetic composition does not include any therapeutic agent.

Process for Making Clay Nanoparticles and Compositions

Also provided herein is a process for making the clay nanoparticles and compositions of the disclosure.

Typically, the process includes combining a lithium salt solution, a magnesium salt solution, a solution including the cationic component and a silicate solution. Such salt solutions to be used in the process of the disclosure can be any suitable aqueous solutions known to the skilled person.

As the lithium salt solution, lithium sulfate solution, lithium chloride solution, lithium hydroxide solution, lithium nitrate solution and combinations thereof, can be used. Typically lithium sulfate solution is used. The process of making the clay nanoparticles and compositions of the disclosure can first involve a step of dissolving a lithium salt in water to form an aqueous solution. The salt can be a hydrated salt, such as a monohydrate. In some embodiments the process involves a step of dissolving lithium sulfate monohydrate in water.

As a magnesium salt solution, magnesium sulfate solution, magnesium chloride solution, magnesium nitrate solution, and combinations thereof, can be used. Typically, magnesium sulfate solution is used. The process of making the clay nanoparticles and compositions of the disclosure can first involve a step of dissolving a magnesium salt in water to form an aqueous solution. The salt can be a hydrated salt, such as a monohydrate or a heptahydrate. In some embodiments the process involves a step of dissolving magnesium sulfate heptahydrate in water.

As a silicate solution, sodium silicate solution, potassium silicate solution, or a combination thereof can be used. Typically, sodium silicate solution is used. The process of making the clay nanoparticles and compositions of the disclosure can first involve a step of dissolving a silicate in water to form an aqueous solution. In some embodiments the process involves a step of dissolving sodium silicate in water.

As a salt solution including the cationic component, any appropriate solution can be used. These include, for example, a carbonate solution, a phosphate solution, a sulfate solution, a nitrate solution, or a combination thereof. Typically a carbonate solution is used, such that when the cationic component includes sodium, a sodium carbonate solution can be used. The process of making the clay nanoparticles and compositions of the disclosure can first involve a step of dissolving the cationic component salt in water to form an aqueous solution. In some embodiments the process of the disclosure includes a step of dissolving sodium carbonate to form an aqueous solution.

Once the solutions have been combined the process of the disclosure typically includes heating the combined solutions together. Heating typically continues until a slurry is formed. The weight % of the solids in the slurry compared to the total weight of the slurry is typically from around 1 wt % to 15 wt %, typically around 3 wt % to 12 wt %. Sometimes, the weight % of the solids in the slurry compared to the total weight of the slurry is from around 3 wt % to around 5 wt %. Sometimes, the weight % of the solids in the slurry compared to the total weight of the slurry is from around 8 wt % to around 10 wt %. The combined solutions are typically heated to the boiling point of the slurry (i.e. to about 100° C.). Heating at this temperature, typically under reflux, is typically continued for a period of from around 30 minutes to around 2 hours, typically about an hour.

The process of the disclosure can include a further step including hydrothermal treatment of the slurry. A hydrothermal treatment as referred to herein, is any treatment including heating of a composition (in this instance a slurry) in the presence of water. For instance, hydrothermal treatment can include autoclaving. Typically, hydrothermal treatment can occur at a temperature of from 60 to 500° C. The hydrothermal treatment can occur at an elevated pressure (i.e. above standard atmospheric pressure (about 100 000 Pa). Hydrothermal treatment at elevated pressure can be referred to as autoclaving. Thus, the process of the disclosure can include an autoclaving step.

Typically, the hydrothermal treatment step occurs at a temperature of from around 100° C. to around 300° C., typically around 150° C. to around 250° C., preferably around 180° C. to around 220° C. Typically the hydrothermal treatment step occurs at a pressure of from 30 psi to around 1800 psi, typically from around 60 psi to around 600 psi, preferably from around 100 psi to around 400 psi. Typically the hydrothermal treatment step lasts for approximately 1 hour to 24 hours, preferably 2 hours to 12 hours, 4 hours to 8 hours, most preferably around 6 hours.

The process of the disclosure can further include a drying step, wherein the slurry is dried to form a solid. Drying of the slurry can be carried out using any appropriate method known to the skilled person, for example rotoevaporation, oven drying or vacuum filtration. Preferably vacuum filtration is used (e.g. using a Buchner funnel).

The process can also include a step of washing and re-drying the dried product. Any appropriate solvent can be used to wash the product. Typically deionised water is used. Vacuum filtration (e.g. using a Buchner funnel) can be used in this step.

The washing step is especially useful to remove soluble salt impurities, such sulfates. To assess if all impurities have been removed, $BaCl_2$ can be added to the filtrate. If a precipitate is formed, typically further washing is required.

Typically, more than one drying method is used, such as vacuum filtration in combination with oven drying. Oven drying typically occurs at a temperature not too far about standard temperature. Typically oven drying occurs at a temperature of from around 40° C. to around 80° C., more typically around 55° C. to around 65° C.

A drying step can last for around 1 hour to 24 hours, typically around 6 hours to 14 hours.

The process of the disclosure can further include a step of grinding the dried product to form a powder. Grinding can occur using any appropriate method, such as use of a pestle and mortar.

The process of the disclosure can further include a step of adding water to the composition to form a gel.

When the water is added to the composition, the composition can be subjected to rigorous stirring, i.e. stirring with a magnetic stirrer at a rate of 300 rpm to 1000 rpm, such as 500 rpm to 800 rpm. The stirring can occur at any temperature, such as from 0° C. to 100° C., or 10° C. to 40° C. Typically the stirring occurs as standard atmospheric temperature and pressure (SATP), such as around 25° C., and around 15 psi.

In some embodiments no further steps are required to obtain the gel. In some embodiments of the process, the gel can then be sterilised, optionally via autoclaving. Autoclaving typically occurs at from around 100° C. to around 140° C., such as around 120° C. Autoclaving typically occurs for between 10 minutes and 1 hour, such as 30 minutes. Autoclaving typically occurs at from 13 psi to 20 psi, such as from 15 psi to 20 psi.

The process of the disclosure can further include a step of adding one or more therapeutic or diagnostic agents to the composition. The one or more therapeutic or diagnostic agents can be added to the composition at any step during the process of the disclosure. The one or more therapeutic or diagnostic agents can also be added to the composition prior to formation of the gel. The one or more therapeutic or diagnostic agents can be added after the composition when it is in the form of a gel, but prior to administration to the subject. The one or more therapeutic or diagnostic agents can alternatively or additionally be administration to the subject separately from the gel, e.g. by administration of the one or more therapeutic or diagnostic agents into the gel in vivo at the target site, or by adding the one or more therapeutic or diagnostic agents as a coating to the gel, in particular when the gel itself is coated on the surface of a medical device, such as an implant, a stent, or a balloon. Typically, the one or more therapeutic or diagnostic agents are added after the composition when it is in the form of a gel, but prior to administration to the subject.

The invention can be further understood by the following numbered paragraphs:

1. A composition including a plurality of clay nanoparticles, wherein each clay nanoparticle includes an anionic component and a cationic component wherein the anionic component has the formula (I):

   $[(Si_8Mg_bLi_c)O_{20}(OH)_4]$     (I)

wherein $5.5 < b \leq 6$,
   and wherein $c > 0$ and $b/c > 12$.
2. A composition according to paragraph 1 wherein $12 < b/c \leq 100$.
3. A composition according to paragraph 1 or paragraph 2 wherein $12 < b/c \leq 18$, preferably wherein $13 < b/c \leq 18$.
4. A composition according to any one of paragraphs 1 to 3, wherein $0.2 \leq c \leq 0.5$.
5. A composition according to any one of paragraphs 1 to 4 wherein the cationic component includes $Na^+$.
6. A composition according to any one of paragraphs 1 to 5, wherein the figures b and c are determined by elemental analysis using inductively coupled plasma-optical emission spectrometry (ICP-OES).
7. A composition according to any one of paragraphs 1 to 6 wherein the average size of the longest dimension of the clay nanoparticles is from about 15 nm to about 50 nm, and wherein the average size of the shortest dimension of the clay nanoparticles is from about 1 nm to about 3 nm.
8. A composition according to any one of paragraphs 1 to 7 which further includes one or more therapeutic or diagnostic agents.
9. A composition according to paragraph 8 wherein the one or more therapeutic or diagnostic agents are therapeutic or diagnostic agents suitable for use in regenerative medicine.
10. A composition according to paragraph 8 or paragraph 9 wherein the one or more therapeutic or diagnostic agents are selected from small molecules, growth factors, antibodies, biological tissue substitutes, synthetic bone grafts, antimicrobial agents, antibiotics and cells.
11. A composition according to any one of paragraphs 1 to 10 wherein the composition includes BMP-2.
12. A composition according to any one of paragraphs 1 to 11 wherein the composition is in a solid form, preferably in a powder form.
13. A composition according to any one of paragraphs 1 to 11 wherein the composition is in the form of a gel or a film.
14. A composition according to paragraph 13 wherein the gel demonstrates a 50% change in zeta potential within a pH range of from pH 6.5 to pH 8, when zeta potential is measured using acid titration.
15. A pharmaceutical composition including a composition according to any one of paragraphs 1 to 14, a pharmaceutically acceptable carrier or diluent, and optionally one or more pharmaceutically acceptable excipients.
16. A kit including a syringe or a vial (e.g. a sprayable vial), wherein the syringe or vial contains a composition according to paragraph 13 or paragraph 14, or a composition according to paragraph 15 wherein the composition is in the form of a gel.
17. A kit including separately a composition according to any one of paragraphs 1 to 7; and one or more therapeutic or diagnostic agents as defined in any one of paragraphs 8 to 11, preferably wherein (a) the composition is in powder form or in the form of a gel; and/or (b) the therapeutic or diagnostic agent is in a powder form.
18. A process for making a composition as described in any one of paragraphs 1 to 15, wherein the process includes combining a lithium salt solution, a magnesium salt solution, a solution including the cationic component and a silicate solution, and heating the solutions together until a slurry is formed.
19. A process according to paragraph 18 wherein the process further includes a hydrothermal treatment step.
20. A process according to paragraph 18 or paragraph 19 wherein the process further includes a step of drying the slurry to form a solid, optionally wherein the process further includes a step of grinding the solid to form a powder.
21. A process according to paragraph 20, wherein the process further includes adding water to the composition to form a gel.
22. A process according to any one of paragraphs 18 to 21 wherein the process further includes a step of adding one or more therapeutic or diagnostic agents to the composition, wherein the one or more therapeutic or diagnostic agents are as defined in any one of paragraphs 8 to 11.
23. A composition according to any one of paragraphs 1 to 15 for use in the treatment of the human or animal body.

24. A composition according to any one of paragraphs 1 to 15, or 23 for use in a method of regenerative medicine.

25. A composition for use according to paragraph 24, wherein the composition is for use in a method of tissue repair or regeneration, and/or cell delivery.

26. A composition according to any one of paragraph 1 to 15, or 23 for use in the treatment or prevention of infection.

27. A composition according to any one of paragraphs 1 to 15, or 23 for use in a method of delivery of one or more therapeutic or diagnostic agents to a target site in the human or animal body, wherein said method includes administering said composition to the human or animal body, wherein the composition includes one or more therapeutic or diagnostic agents and/or wherein one or more therapeutic or diagnostic agents are administered separately into the composition in vivo at the target site.

28. A cosmetic composition including a composition according to any one of paragraphs 1 to 14 and optionally one or more additives, preferably wherein the cosmetic composition is a tissue filler or a topical gel or cream.

EXAMPLES

Example 1—Synthesis of Clay Nanoparticles 2.65 g of $Li_2SO_4 \cdot H_2O$ was dissolved into 170 mL of de-ionised water at room temperature using a stirrer. Once the $Li_2SO_4 \cdot H_2O$ was dissolved, 56.10 g of $MgSO_4 \cdot 7H_2O$ was added. The mixed salt solution was then transferred to a round bottom flask (RBF) in an assembled reactor which was heated to 60±10° C.

21.95 g of $Na_2CO_3$ was dissolved in a separate vessel into 130 mL DI water, at room temperature and under stirring.

When the RBF contents had reached 60° C. (±10° C.), the $Na_2CO_3$ solution was added using a stoppered self-equalising dropping funnel at roughly 1 drop a second.

Using a fresh dropping funnel, 69.7 g of sodium silicate solution was then added to the RBF at roughly 1 drop a second.

A reflux condenser was then fitted to the reactor and the temperature of the reactor increased to 100° C. The mixed salt solution was then allowed to boil under reflux at atmospheric pressure for 1 hour.

After one hour, the reaction mixture was then reduced to 60° C., keeping all other conditions unchanged. A resultant slurry has been formed.

An oven was pre-heated to 200° C., with the fan set to maximum and the damper to 40%.

The slurry is transferred into autoclave vessels (120 mL per vessel). The autoclave vessels were then placed in the oven for hydrothermal treatment (HT) at 200° C. for 6 hrs. The oven was then switched off and the vessels allowed to cool.

Once cooled the slurry was washed from the autoclave vessels. The contents of each autoclave vessel was then transferred individually into a Buchner funnel, and the filter cake washed with de-ionised water. 400 mL of de-ionised water were used per autoclave vessel.

The Buchner flask was regularly emptied and the filtrate tested with $BaCl_2$ solution. If a precipitate formed, it indicated that sulfate was still being washed from the filter cake. Further washing was continued until no precipitate formed.

The filter cake was then transferred into a vessel suitable for the drying procedure. The filter cake was then left to dry for at least 8 to 12 hours, but could be left for up to 72 hours. Drying occurred in an oven set at 60° C. at 100% fan, and 40% damper.

The dried filter cake was then ground for about 10 minutes into a powder using a mortar and pestle to achieve fine particles.

Example 2—Chemical Composition of the Clay Nanoparticles

The composition of the clay nanoparticles prepared using the method of Example 1 was then analysed by elemental analysis using inductively coupled plasma-optical emission spectrometry (ICP-OES). Laponite™ XLG was also assessed using the same method. The results are summarised in the below Table 1 where empirically determined Mg, Li and Na are presented relative to empirically determined Si which is scaled according to the following chemical formula ratio $(Na^+)_a[(Si_8Mg_bLi_d)O_{20}(OH)_4]^{-a}$. The results are summarised in the below Table 1:

TABLE 1

| Sample | Numbers relating to formulae I and II | | | | Mg/Si ratio | Li/Si ratio | Mg/Li ratio |
| --- | --- | --- | --- | --- | --- | --- | --- |
| | Si | Mg (b) | Na (a) | Li (d) | | | |
| Laponite ™ | 8.00 | 5.40 | 0.79 | 0.48 | 0.68 | 0.060 | 11.24 |
| AS-13 | 8.00 | 5.84 | 0.46 | 0.41 | 0.73 | 0.055 | 12.35 |
| AS-14 | 8.00 | 5.83 | 0.46 | 0.41 | 0.73 | 0.046 | 12.35 |
| AS-15 | 8.00 | 5.84 | 0.42 | 0.34 | 0.73 | 0.058 | 15.15 |
| AS-18 | 8.00 | 5.85 | 0.38 | 0.36 | 0.73 | 0.054 | 14.49 |
| AS-19 | 8.00 | 5.96 | 0.45 | 0.35 | 0.75 | 0.046 | 13.51 |

The comparison of elemental ratios between Laponite™ and the compositions set out in Table 1 (collectively referred to as Renovite) are also displayed graphically in FIG. 1.

Figure 2:
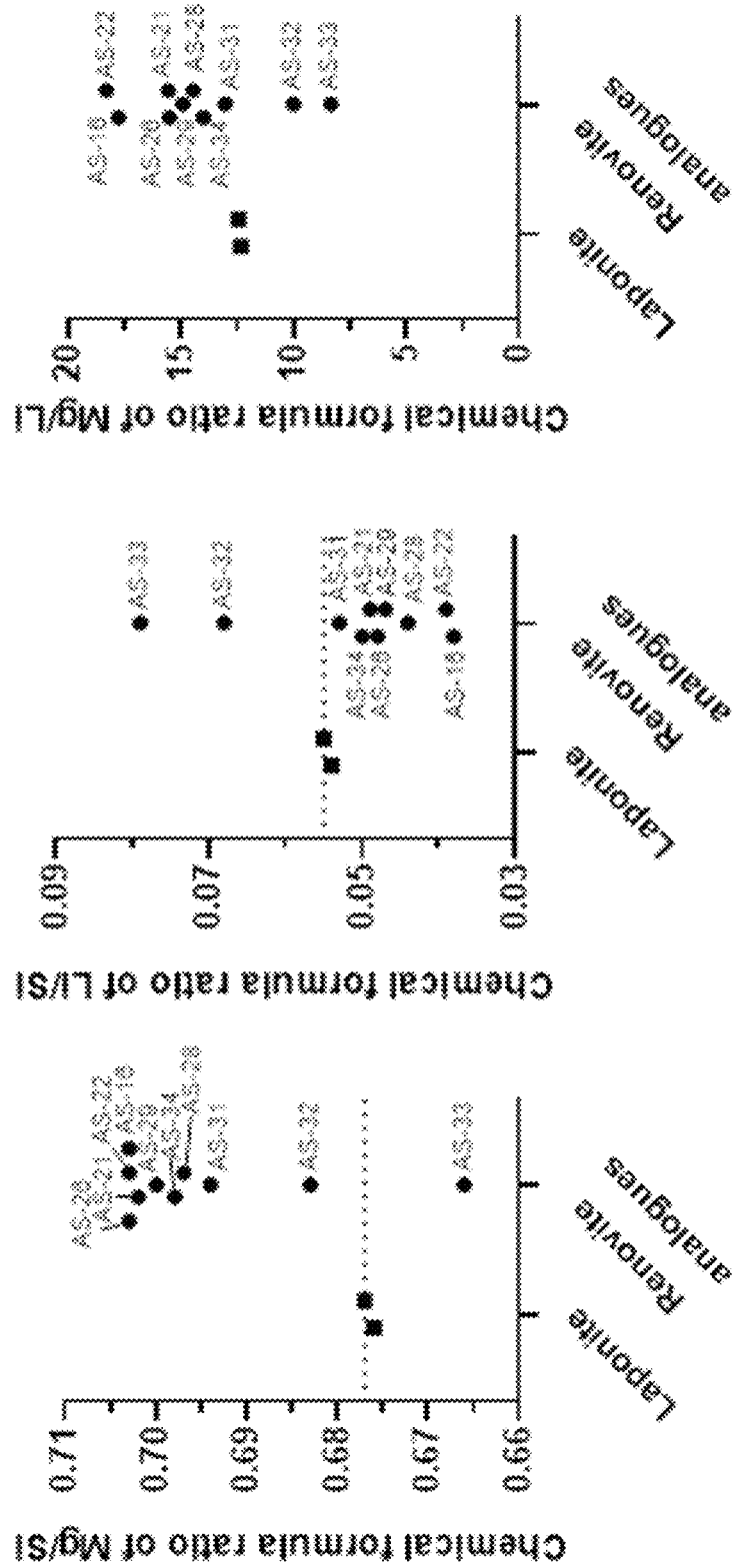
FIG. 2 shows comparison of elemental ratios between Laponite™ XLG and a range of compositions of the disclosure as set out in Table 2 (Renovite analogues). Mg content calculated from empirical Si, Li and Na values on basis of the formula: $(Na_{+a}[(Si_8Mg_bLi_d)O_{20}(OH)_4]^{-a}$. Bars represent mean.

To exemplify further variation in elemental composition of the nanoclay of the disclosure, the method of Example 1 was repeated with variation in the synthesis protocol as set out in Table 2 below. For each modified synthesis, ICP-OES analysis data for of the resulting nanoclay is provided and elemental ratios for Mg/Si and Mg/Li in contrast to Laponite™ are presented in FIG. 2.

TABLE 2

| Sample | Synthesis variable | Numbers relating to formulae I and II | | | | Mg/Si ratio | Li/Si ratio | Mg/Li ratio |
| --- | --- | --- | --- | --- | --- | --- | --- | --- |
| | | Si | Mg (b)* | Na (a) | Li (d) | | | |
| AS-16 | 0.875 × HT temp | 8.00 | 5.62 | 0.45 | 0.31 | 0.703 | 0.038 | 18.18 |
| AS-21 | 2 × Li | 8.00 | 5.63 | 0.38 | 0.36 | 0.702 | 0.049 | 15.63 |
| AS-22 | 0.75 × Li | 8.00 | 5.62 | 0.44 | 0.32 | 0.703 | 0.039 | 17.86 |
| AS-26 | 1.5 × Li | 8.00 | 5.62 | 0.41 | 0.36 | 0.703 | 0.044 | 15.63 |
| AS-28 | 0.66 × HT time | 8.00 | 5.57 | 0.47 | 0.39 | 0.697 | 0.048 | 14.49 |

TABLE 2-continued

| | | | | | | Numbers relating to formulae I and II | | |
|---|---|---|---|---|---|---|---|---|
| Sample | Synthesis variable | Si | Mg (b)* | Na (a) | Li (d) | Mg/Si ratio | Li/Si ratio | Mg/Li ratio |
| AS-29 | 1.33 × HT time | 8.00 | 5.60 | 0.42 | 0.38 | 0.7 | 0.047 | 14.93 |
| AS-31 | Standard synthesis | 8.00 | 5.55 | 0.47 | 0.43 | 0.694 | 0.053 | 12.99 |
| AS-32 (reference sample) | 0.9 × Mg | 8.00 | 5.46 | 0.52 | 0.55 | 0.683 | 0.068 | 10.00 |
| AS-33 (reference sample | 0.8 × Mg | 8.00 | 5.32 | 0.72 | 0.64 | 0.666 | 0.079 | 8.40 |
| AS-34 | Ultra-pure water | 8.00 | 5.58 | 0.44 | 0.40 | 0.698 | 0.050 | 14.08 |
| Laponite ™ | | 8.00 | 5.42 | 0.73 | 0.44 | 0.678 | 0.055 | 12.35 |

*Mg content calculated from empirical Si, Li and Na values on basis of formula I; HT = hydrothermal treatment.

Example 3—Protocol for Producing Gels

Gels of the disclosure are prepared as a weight percentage (wt. %) of nanoclay/water where 1% is equivalent to 1 g/100 ml or 10 mg/ml. Gels were prepared using the nanoclays of the disclosure at concentrations in the range 2 to 7 wt %. Reference gels were also prepared using corresponding amounts of Laponite™ as the nanoclay, for comparison purposes. The mixing procedure is designed to ensure complete wetting out and dispersion of the clay particles.
1) Deionised water (18.2 MΩ, pH 7) is added into a glass bottle with a magnetic stirrer bar and place on a stirrer to generate a stable vortex that extends close to the base of the bottle but without exposing the stirrer to air.
2) Powdered nanoclay is added gradually into the vortex over the course of 5-10 seconds.
3) The suspension is left to stir for 1-2 mins at room temperature before being briefly mixed on a vortex to remove any powder stuck on the sides or forming clumps. Stirring is continued for a further 25 mins, until the colloidal solution is clear.
4) The total weight of the bottle containing the gel is measured before undergoing autoclave sterilisation for ~30 min at 121° C. and 15 psi using a bench top autoclave suitable for liquid sterilization. Once it has cooled, the bottle is weighed again and any lost water replaced followed by mixing on a vortex. To keep the gel of the disclosure sterile, handling is under sterile conditions and sterile deionized water used to replace lost water.

Example 4: Rheometric Measurements and Gelation Response to Blood Serum

The rheological properties of gels of the disclosure were characterised both in their native state and following addition to a bath of simulated blood serum (40 mg/ml bovine serum albumin in phosphate buffered saline, pH 7.4) to assess their response in physiological solutions (such as, for example, following injection into the body).

Figure 3:
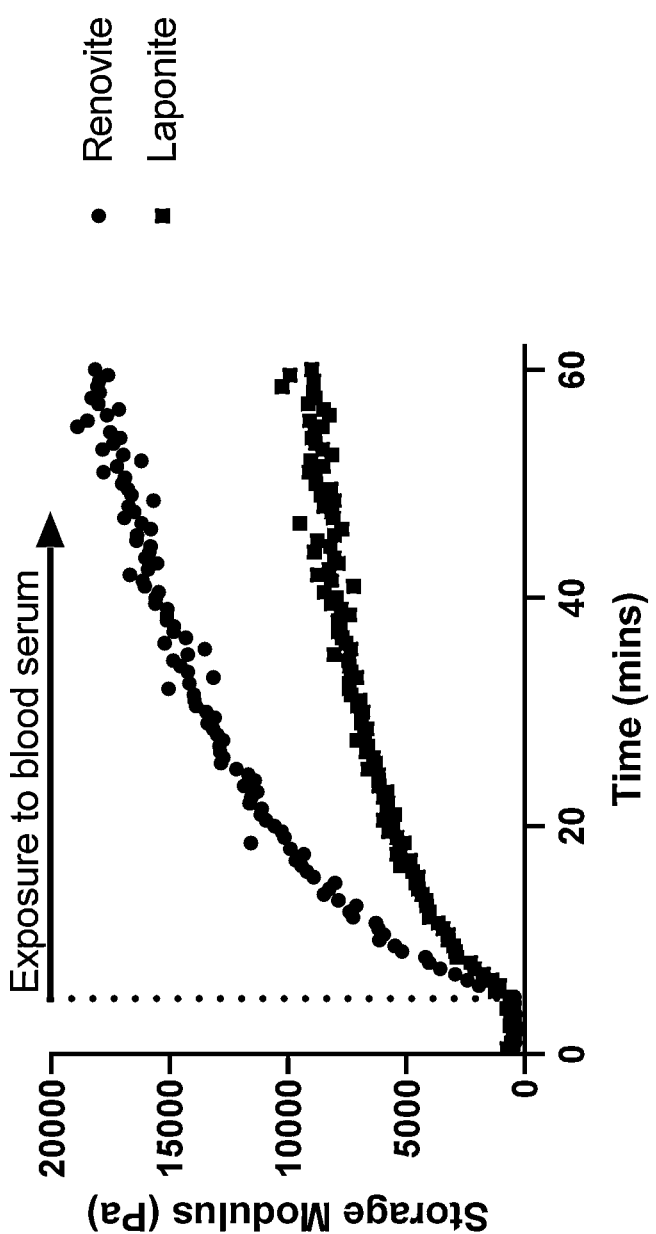
FIG. 3 shows enhanced gelation of Renovite (AS-19, Table 1) in response to blood serum. Rheometric isotherm of changes in gel stiffness (storage modulus) in Renovite vs Laponite™ (XLG) suspensions following exogenous exposure to simulated blood serum (40 mg/ml bovine serum albumin in phosphate buffered saline, pH 7.4). With exposure to simulated blood serum, the observed increase in gel stiffness was enhanced in Renovite. Measurements taken at 25° C.

All rheological measurements were conducted on an MCR 92 rheometer (Anton Paar, UK) using a 12 mm parallel plate geometry (PP12 probe) where 117 µl gel suspensions were loaded onto the rheometer plate pre-set to 25° C. with a 1 mm gap. Isotherm measurements of storage and loss modulus in response to blood serum over time were taken over 60 min at a constant oscillatory strain of 0.005% and angular frequency of 1 rad s$^{-1}$. After 5 minutes a serum reservoir was applied up to the level of the lower surface of the upper plate. FIG. 3 shows that the observed increase in storage modulus in response to serum addition was enhanced in gels of the disclosure compared with Laponite™ gels having a corresponding nanoclay concentration.

Figures 4A, 4B:
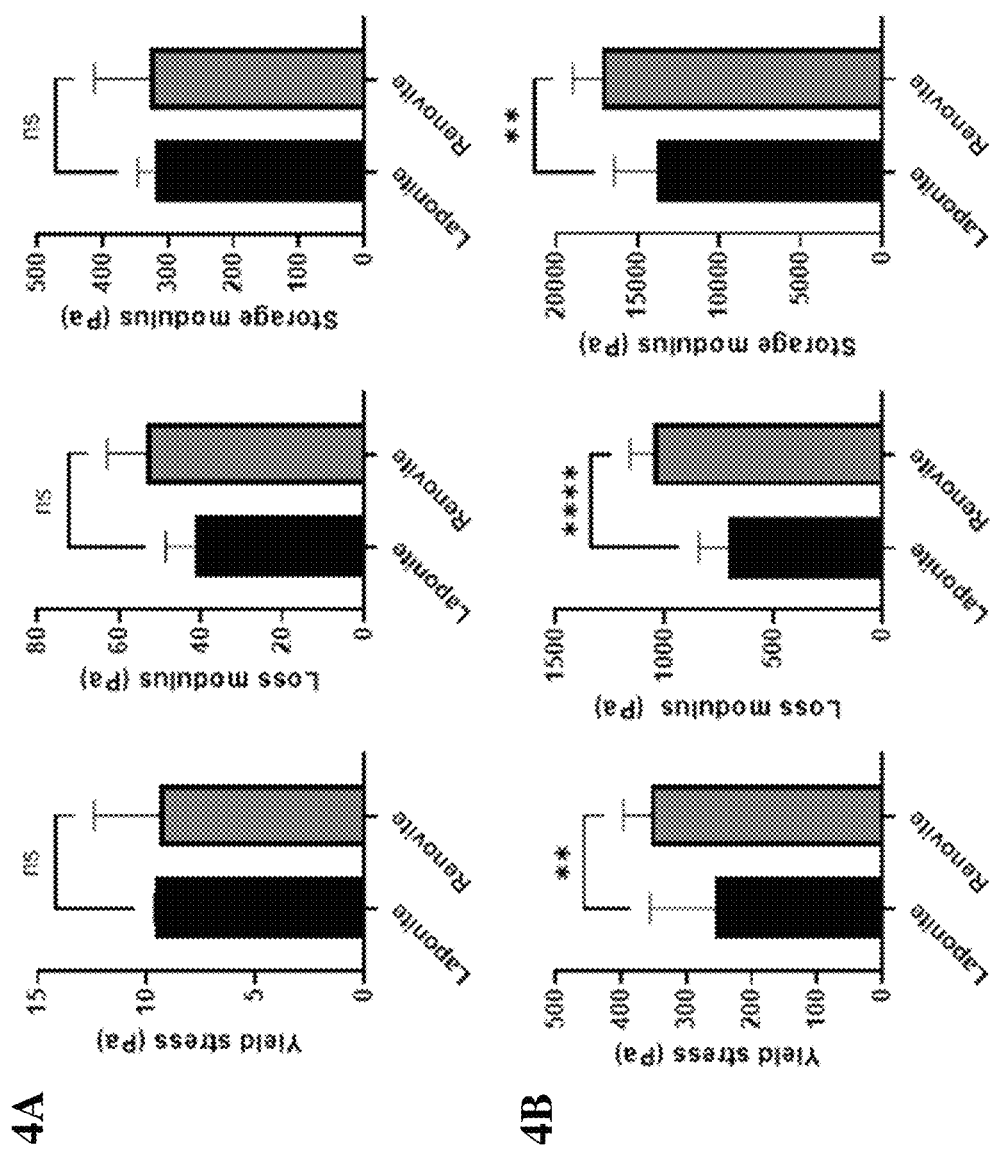
FIGS. 4A-4B show enhanced gelation of compositions of the disclosure (Renovite: mean of all clay batches listed in Table 1) in response to blood serum. Rheometric analysis of Renovite vs Laponite™ (XLG) suspensions in their native state (FIG. 4A) and after 1-hour exogenous exposure to simulated blood serum (FIG. 4B; 40 mg/ml bovine serum albumin in phosphate buffered saline, pH 7.4). Renovite displayed equivalent gel strength (yield stress (Pa)), stiffness (storage modulus (G')) and viscosity (storage modulus (G")) to XLG in its native state. With exposure to simulated blood serum, the observed increase in gel strength, stiffness and viscosity was significantly enhanced in Renovite. Yield stress was calculated as the point of inflection (>5%) from the linear dependence of shear stress on shear strain. Histograms plot mean values. Error bars=SD, N=6, , and ** indicate $P<0.01$ and $P<0.0001$, respectively (unpaired t-test).
Figure 5A:
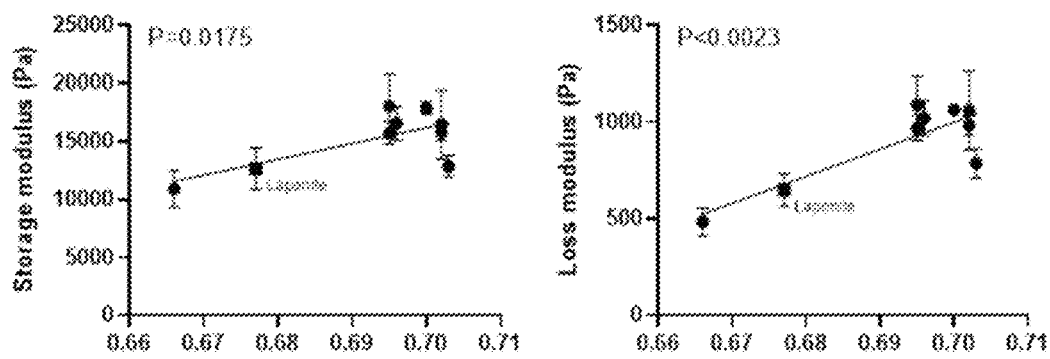
FIGS. 5A-5C show enhanced gelation of compositions of the disclosure (AS-13, 14, 15, 18, 19, 21, 22, 33) in response to blood serum correlates with Mg and Li content. Storage and loss modulus of high and low Mg/Li compositions of the disclosure and reference samples as set out in Table 2 vs Laponite™ (XLG) suspensions after 1-hour exogenous exposure to simulated blood serum shows a significant positive correlation with Mg/Si (FIG. 5A) a significant negative correlation with Li/Si (FIG. 5B) and a slight positive trend association with Mg/Li molar ratios (FIG. 5C). Mg content calculated from empirical Si, Li and Na values on basis of the formula: $(Na_{+a}[(Si_8Mg_bLi_d)O_{20}(OH)^4]^{-a}$. P values report Pearson's correlation coefficients where a significant correlation is $P<0.05$. ns=not significant.
Figure 5B:
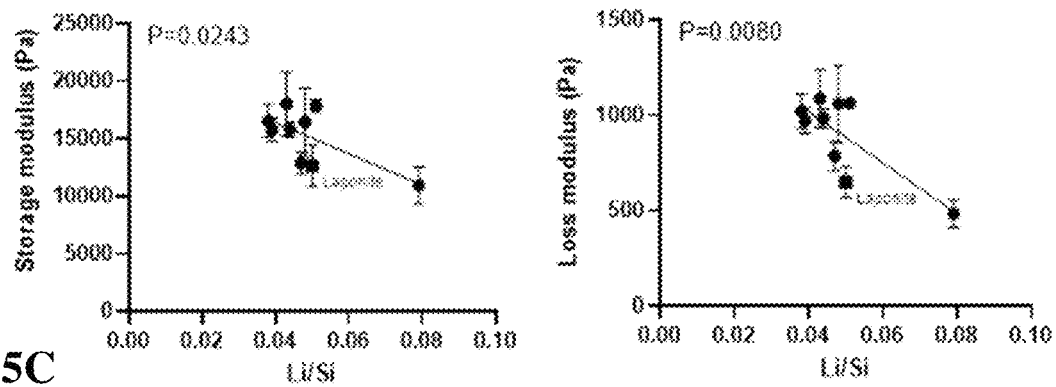
Figure 5C:
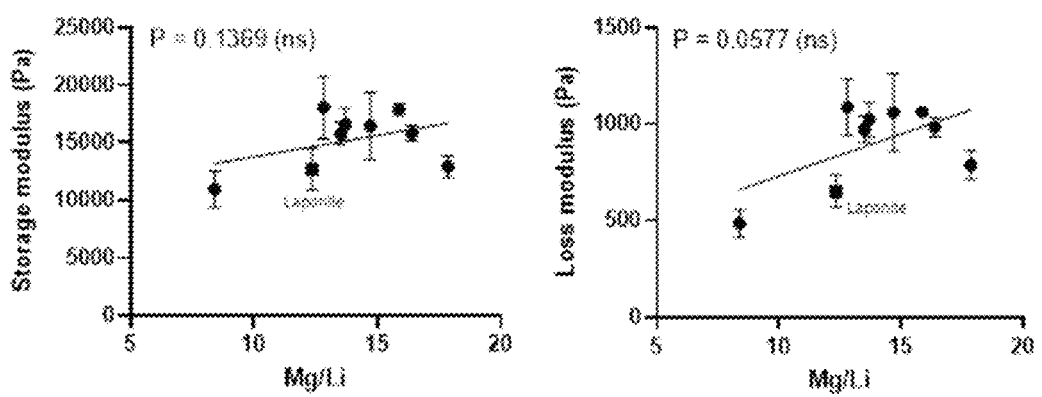

Amplitude sweeps covering the range of 0.01-100% strain were applied to measure storage and loss modulus within the linear viscoelastic range (LVR) and to define yield strain and stress, again at a constant angular frequency of 1 rad s$^{-1}$. To calculate yield stress and yield strain, elastic stress (τ) was plotted against shear strain (γ) and yield stress and yield strain for each treatment calculated as the point of inflection (>5%) from the linear dependence of τ on γ. FIGS. 4A-4B show that, in its native state, a gel of the disclosure can possess equivalent gel strength (yield stress (Pa)), stiffness (storage modulus (G')) and viscosity (storage modulus (G")) to a Laponite™ gel having a corresponding nanoclay concentration (FIG. 4A, top), but in simulated blood serum, the increase in gel strength, stiffness and viscosity was significantly enhanced in gels of the disclosure (FIG. 4B, bottom). FIGS. 5A-5C reports storage and loss modulus of a range of high and low Li/Mg gels of the disclosure and their analogues vs Laponite™ suspensions in simulated blood serum and show a significant positive correlation with Mg/Si (FIG. 5A), a significant negative correlation with Li/Si (FIG. 5B), and a slight positive trend association with Mg/Li molar ratios (FIG. 5C) molar ratios across the various nanoclays.

Example 5: Protocol for Measuring Zeta Potential Half Maximum (PHM) and Gelation Response to pH Gels of the disclosure prepared according to Example 3 were measured to assess zeta-potential kinetics in response to pH. Zeta potential is the electrical potential at the slipping plane. This plane is the interface which separates mobile fluid from fluid that remains attached to the surface. Zeta potential describes the electrokinetic potential in colloidal dispersions and is a function of the specific surface chemistry of a dispersion which are affected by changes in pH, salt, and surfactant concentration. At its minimum zeta potential (i.e. its absolute lowest value) a colloid is a its most stable as a dispersion due to the dominance of repulsive over attractive interactions between particles. As the zeta potential approaches the isoelectric point attractive interactions increase resulting in aggregation of particles.

Titrations using 1M HCL (30 ul at 20 second intervals) were performed on the Stabino™ II kit allowing dynamic measurement of zeta potential (P) with falling pH. All titrations were performed on 1 wt. % solutions of clay in filtered ultrapure water, prepared on the day of testing.

Figure 6:
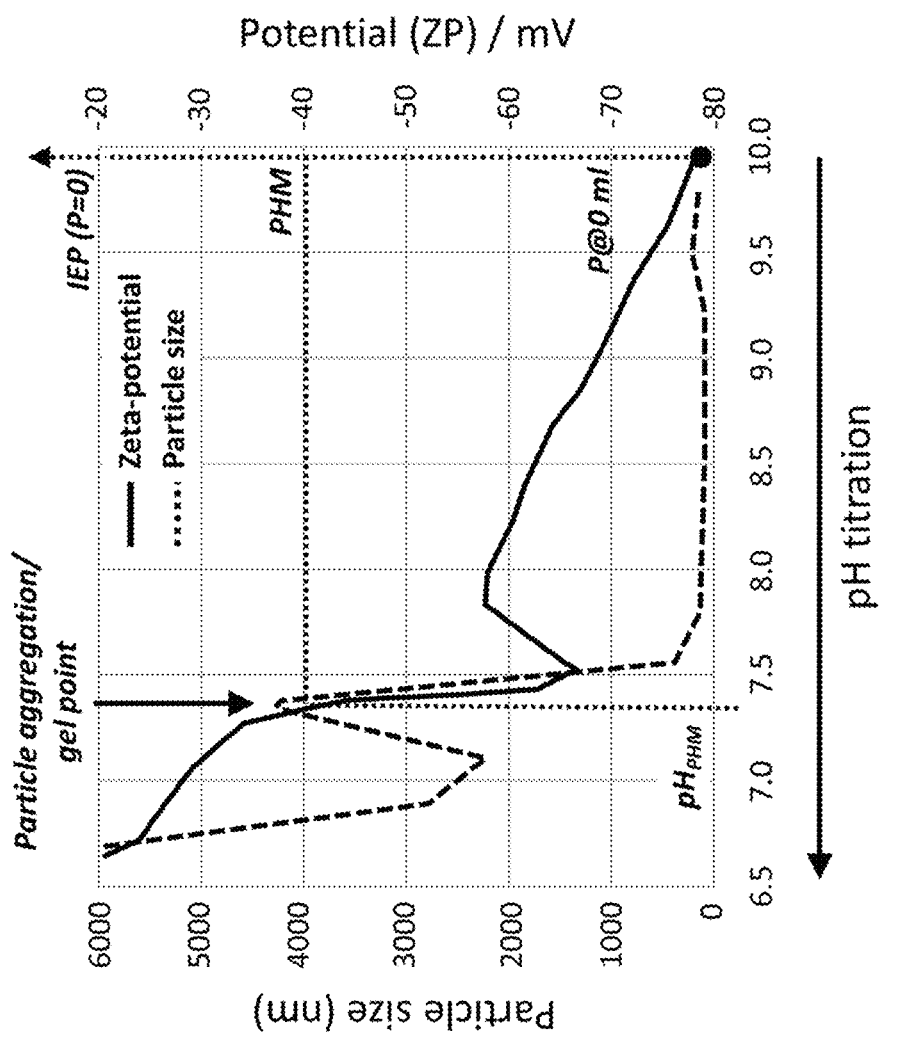
FIG. 6 shows Zeta Potential Half Maximum (PHM) and its significance for nanoclay gelation. A sharp decrease in negative zeta potential (ZP) of nanoclays (here, AS-14) is observed between pH8 and pH5 over the course of titration with HCL. This sharp decrease in negative ZP coincides with an increase in particle (aggregate) size. This indicates a phase-transition from repulsive to attractive particle interactions which under diffusion and at high nanoclay concentrations (>2 wt %) yields a gel. $pH_{PHM}$ represents the pH at which this sharp decrease in negative ZP occurs by measuring the pH at which negative ZP is 50% of its recorded mV prior to addition of titrant. Titrations and dynamic ZP measurements were performed on the Stabino™ II device programmed to add 30 µl of 1M HCL every 20 seconds.
Figure 7:
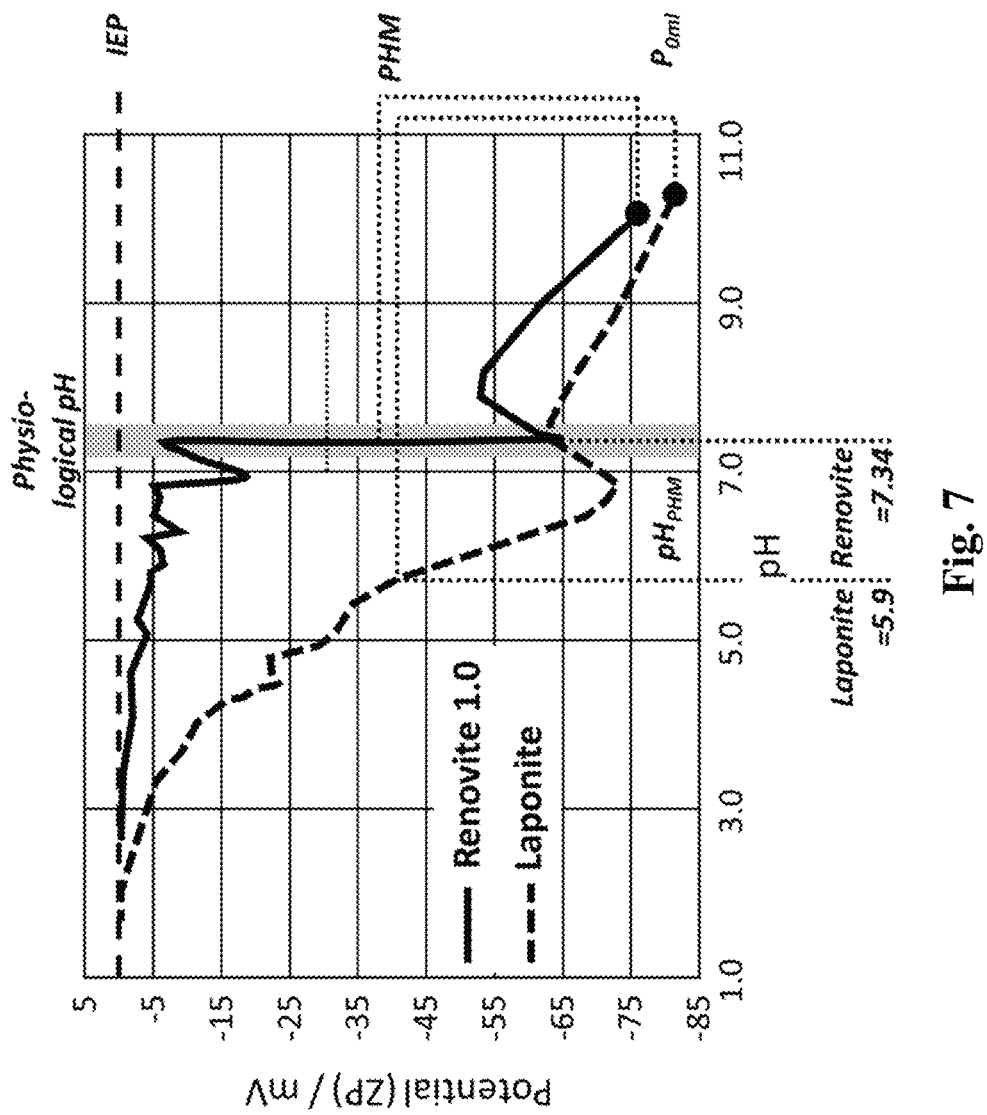
FIG. 7 shows Zeta Potential Half Maximum (PHM) for a composition of the disclosure (AS-14, labelled Renovite 1.0) versus Laponite™. The PHM for Renovite occurs near physiological pH7.4 (shaded grey) compared with pH 5.9 in Laponite™. Titrations and dynamic ZP measurements were performed on the Stabino™ II programmed to add 30 µl of 1M HCL every 20 seconds to a suspension of 1 wt % nanoclay.
Figure 8:
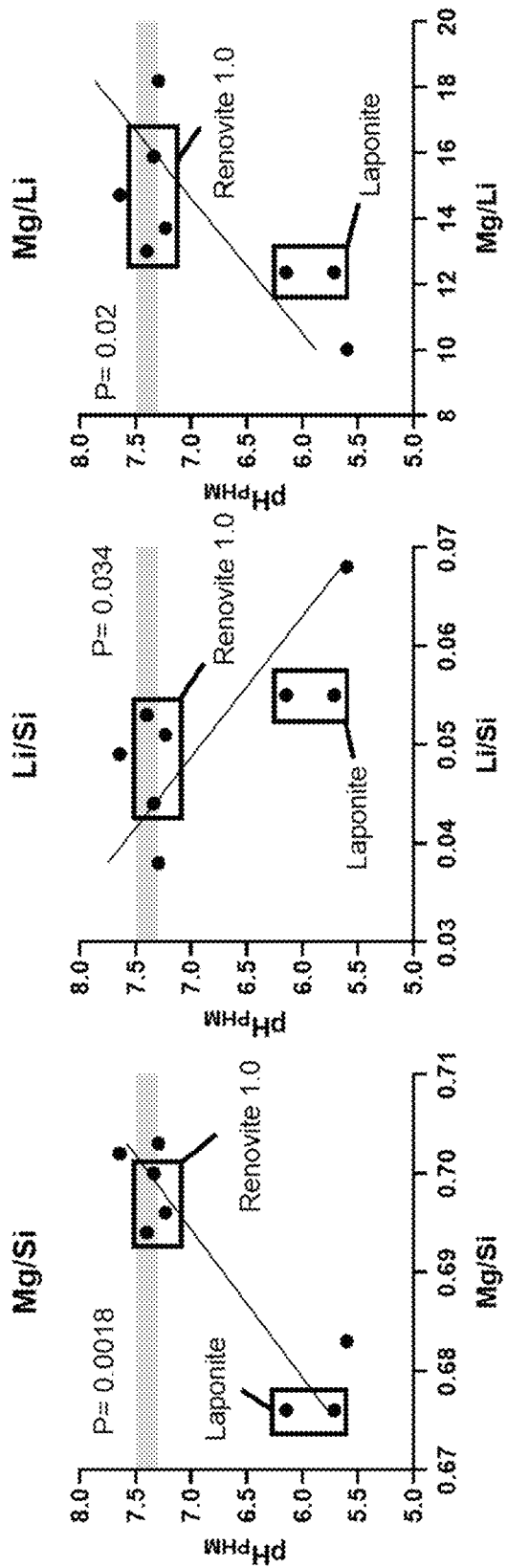
FIG. 8 shows Zeta Potential Half Maximum (PHM) correlates with Mg and Li content. pH at PHM ($pH_{PHM}$) for 1 wt % high and low Mg/Li compositions of the disclosure (AS-13, 14, 15, 18, 19, 21, 22, labelled Renovite 1.0), and reference sample AS-33 vs Laponite™ (XLG) suspensions. A significant positive correlation with Mg/Si and Mg/Li and a significant negative correlation with Li/Si was observed. $pH_{PHM}$ for Renovite 1.0 occurred at pH values approximating physiological pH 7.4 (shaded grey). Mg content calculated from empirical Si, Li and Na values on basis of the formula: $(Na_{+a}[(Si_8Mg_bLi_d)O_{20}(OH)_4]^{-a}$. P values report Pearson's correlation coefficients where a significant correlation is $P<0.05$.

FIG. 6 shows the sharp decrease in negative zeta potential (ZP) occurring between pH8 and pH5 over the course of titration with HCl. This was a characteristic feature of all nanoclays tested and coincided with an increase in particle (aggregate) size indicating a transition from repulsive to attractive particle interactions. At high nanoclay concentrations (>2 wt %) an increase in attractive interactions yields a gel. The pH at which this sharp decrease in potential occurred corresponded with the zeta potential half maximum (PHM) defined as the point at which negative ZP is 50% of its recorded mV prior to addition of titrant. FIG. 7 shows that the pH at which the PHM occurs ($pH_{PHM}$) for gels of the disclosure averages at 7.33—close to physiological pH. This is in contrast to Laponite™ which had a much lower average $pH_{PHM}$ of 5.9. FIG. 8 shows, as with the improved rheological response to serum, the physiologically optimised $pH_{PHM}$ of gels of the disclosure correlates with its higher Mg and lower Li content compared with Laponite™ and other high Li analogues of the gels of the disclosure.

The invention claimed is:

1. A composition comprising a plurality of clay nanoparticles, wherein each clay nanoparticle comprises an anionic component and a cationic component wherein the anionic component has the formula (I):

$$[(Si_8Mg_bLi_c)O_{20}(OH)_4] \qquad (I)$$

wherein 5.5<b≤6,
wherein c>0;
wherein 12<b/c≤18; and
wherein the composition can form into a gel which demonstrates a 50% change in zeta potential within a pH range of from pH 6.5 to pH 8, when zeta potential is measured using acid titration.

2. The composition of claim 1, wherein 0.2≤c≤0.5.

3. The composition of claim 1 wherein the cationic component comprises $Na^+$.

4. The composition of claim 1, wherein 0.2≤c≤0.5 and wherein the cationic component comprises $Na^+$.

5. The composition of claim 1 further comprising one or more therapeutic or diagnostic agents.

6. The composition of claim 1, wherein 0.2≤c≤0.5, wherein the cationic component comprises $Na^+$, and wherein the composition further comprises one or more therapeutic or diagnostic agents.

7. The composition of claim 5, wherein the one or more therapeutic or diagnostic agents are therapeutic or diagnostic agents suitable for use in regenerative medicine.

8. The composition of claim 6, wherein the one or more therapeutic or diagnostic agents are therapeutic or diagnostic agents suitable for use in regenerative medicine.

9. The composition of claim 5, wherein the one or more therapeutic or diagnostic agents are selected from small molecules, growth factors, antibodies, biological tissue substitutes, synthetic bone grafts, antimicrobial agents, antibiotics and cells.

10. The composition of claim 6, wherein the one or more therapeutic or diagnostic agents are selected from small molecules, growth factors, antibodies, biological tissue substitutes, synthetic bone grafts, antimicrobial agents, antibiotics and cells.

11. The composition of claim 1, wherein the composition comprises BMP-2.

12. The composition of claim 1, wherein 0.2≤c≤0.5, wherein the cationic component comprises $Na^+$, and wherein the composition further comprises BMP-2.

13. The composition of claim 1, wherein the composition is in the form of a gel.

14. The composition of claim 13, wherein 0.2≤c≤0.5, and wherein the cationic component comprises $Na^+$.

15. The composition of claim 13, wherein the composition further comprises one or more therapeutic or diagnostic agents.

16. The composition of claim 15, wherein the one or more therapeutic or diagnostic agents are therapeutic or diagnostic agents suitable for use in regenerative medicine.

17. The composition of claim 15, wherein the one or more therapeutic or diagnostic agents are selected from small molecules, growth factors, antibodies, biological tissue substitutes, synthetic bone grafts, antimicrobial agents, antibiotics and cells.

18. The composition of claim 13, wherein the composition further comprises BMP-2.

19. The composition of claim 1, wherein the composition is in the form of a film.

20. The composition of claim 1, wherein the 50% change in zeta potential is within a pH range of from pH 7 to pH 7.8.

21. The compositions of claim 1, wherein the amounts of magnesium and lithium are measured by inductively coupled plasma-optical emission spectrometry (ICP-OES).

* * * * *